US007332347B2

(12) United States Patent
Li et al.

(10) Patent No.: US 7,332,347 B2
(45) Date of Patent: Feb. 19, 2008

(54) APPARATUS AND METHOD FOR CONCENTRATING AND COLLECTING ANALYTES FROM A FLOWING LIQUID STREAM

(75) Inventors: Liang Li, 814 Twin Brooks Close, Edmonton, Alberta (CA) T6J 7G4; Boyan Zhang, Foster City, CA (US); Alan Austin Doucette, Edmonton (CA)

(73) Assignee: Liang Li, Edmonton, Alberta (CA)

( * ) Notice: Subject to any disclaimer, the term of this patent is extended or adjusted under 35 U.S.C. 154(b) by 619 days.

(21) Appl. No.: 10/414,254

(22) Filed: Apr. 14, 2003

(65) Prior Publication Data
US 2004/0203175 A1 Oct. 14, 2004

(51) Int. Cl.
*B01D 1/02* (2006.01)
*B01D 1/06* (2006.01)
*B01D 1/14* (2006.01)

(52) U.S. Cl. ............... 436/177; 436/161; 436/174; 436/180; 422/70; 422/99; 422/100; 422/101; 73/863.11; 159/43.1

(58) Field of Classification Search ............ 436/174, 436/177, 180, 161; 422/70, 99–101; 73/863.11, 73/8; 159/43.1
See application file for complete search history.

(56) References Cited

U.S. PATENT DOCUMENTS 3,476,291 A 11/1969 Glaser ................. 222/14

(Continued)

FOREIGN PATENT DOCUMENTS
WO WO 01/33605 5/2001

OTHER PUBLICATIONS

Wall, D.B., et al., "Continuous sample deposition from reversed-phase liquid chromatography to tracks on a matrix-assisted laser desorption/ionization precoated target for the analysis of protein digests" Electrophoresis, 2002, 23 (18), 3193-3204.

(Continued)

*Primary Examiner*—Jan M. Ludlow
(74) *Attorney, Agent, or Firm*—Greenlee, Winner and Sullivan, P.C.

(57) ABSTRACT

An apparatus for concentrating and collecting one or more analytes in a flowing liquid stream of a carrier solvent composed of one or more solvent components is provided, which includes a transfer tube which forms a bore having an inlet and an outlet, the inlet being adapted to accept the flowing liquid stream, and the outlet being adapted to form continuously replaced, hanging droplets of the liquid stream, and a collection device mounted below the outlet of the transfer tube for collecting the droplets. The apparatus includes a device for heating the liquid stream in the transfer tube to a temperature sufficient to cause partial evaporation of the carrier solvent from the hanging droplets but not exceeding the boiling point of the carrier solvent, and a device for heating the collection device to a temperature sufficient to cause further evaporation of the carrier solvent from the collected droplets. Also provided is a method for concentrating and collecting one or more analytes in a flowing liquid stream of a carrier solvent composed of one or more solvent components. The method includes the steps of introducing the liquid stream into a transfer tube which forms a bore having an inlet and an outlet, the inlet being adapted to accept the flowing liquid stream, and the outlet being adapted to form continuously replaced, hanging droplets of the liquid stream, and heating the liquid stream in the transfer tube while controlling the temperature of the liquid stream in the transfer tube to be sufficient to cause partial evaporation of the carrier solvent from the hanging droplets without exceeding the boiling point of the carrier solvent. The method allows the droplets to dislodge from the outlet, and the droplet is collected on a collection device mounted below the outlet of the transfer tube. The collection device is also heated to a temperature sufficient to cause further evaporation of the carrier solvent from the collected droplets.

35 Claims, 8 Drawing Sheets

U.S. PATENT DOCUMENTS

| | | | |
|---|---|---|---|
| 3,889,538 A * | 6/1975 | Fingerle | 73/863.11 |
| 3,895,758 A * | 7/1975 | Thoden | 239/296 |
| 4,281,246 A | 7/1981 | White et al. | 250/282 |
| 4,300,044 A | 11/1981 | Iribarne et al. | 250/282 |
| 4,740,298 A | 4/1988 | Andresen et al. | 210/198.3 |
| 4,823,009 A | 4/1989 | Biemann et al. | 250/341 |
| 4,843,243 A | 6/1989 | Biemann et al. | 250/341 |
| 4,968,885 A | 11/1990 | Willoughby | 250/288 |
| 5,039,614 A | 8/1991 | Dekmezian et al. | 436/43 |
| 5,162,650 A | 11/1992 | Bier | 250/288 |
| 5,171,989 A | 12/1992 | Williams et al. | 250/288 |
| 5,223,131 A | 6/1993 | Apffel, Jr. et al. | 210/198.2 |
| 5,238,653 A | 8/1993 | Bourne | 422/70 |
| 5,268,303 A | 12/1993 | Bourne | 436/161 |
| 5,345,079 A | 9/1994 | French et al. | 250/288 |
| 5,447,553 A | 9/1995 | Apffel, Jr. et al. | 95/32 |
| 5,514,336 A | 5/1996 | Fox | 422/64 |
| 5,538,643 A | 7/1996 | Kallos et al. | 210/656 |
| 5,674,388 A | 10/1997 | Anahara | 210/198.2 |
| 5,732,476 A | 3/1998 | Paré | 34/265 |
| 5,762,877 A | 6/1998 | Brewer | 422/100 |
| 5,770,272 A | 6/1998 | Biemann et al. | 427/421 |
| 5,772,964 A | 6/1998 | Prevost et al. | 422/70 |
| 5,859,432 A | 1/1999 | Kato et al. | 250/288 |
| 5,916,524 A | 6/1999 | Tisone | 422/100 |
| 5,917,185 A | 6/1999 | Yeung et al. | 250/288 |
| 6,140,639 A | 10/2000 | Gusev et al. | 250/288 |
| 6,149,815 A | 11/2000 | Sauter | 210/635 |
| 6,175,112 B1 | 1/2001 | Karger et al. | 250/288 |
| 6,203,759 B1 | 3/2001 | Pelc et al. | 422/100 |
| 6,245,227 B1 | 6/2001 | Moon et al. | 210/198.2 |
| 6,248,239 B1 | 6/2001 | Hsi et al. | 210/656 |
| 6,297,499 B1 | 10/2001 | Fenn | 250/288 |
| 6,339,218 B1 | 1/2002 | Kato et al. | 250/288 |
| 6,396,057 B1 | 5/2002 | Jarrell et al. | 250/288 |
| 6,402,947 B1 | 6/2002 | Altamirano et al. | 210/198.2 |
| 6,508,986 B1 | 1/2003 | Anderson et al. | 422/100 |
| 6,722,872 B1 * | 4/2004 | Swanson et al. | 425/225 |
| 2001/0033809 A1 | 10/2001 | Karger et al. | 422/70 |
| 2002/0045270 A1 | 4/2002 | Schurenberg et al. | 436/174 |
| 2002/0051738 A1 | 5/2002 | Schurenberg et al. | 422/102 |
| 2002/0092366 A1 | 7/2002 | Brock et al. | 73/863.32 |
| 2003/0148538 A1 * | 8/2003 | Ng | 436/180 |

OTHER PUBLICATIONS

Hiraoka, K., et al., "A New Liquid Chromatography/Mass Spectrometry Interface: Laser Spray" Rapid Comm. Mass. Spectrom. 1998, 12 (17), 1170-1174.

Zhou, S., and K.D. Cook, "Probing Solvent Fractionation in Electrospray Droplets with Laser-Induced Fluorescence of a Solvatochromic Dye" Anal. Chem. 2000, 72 (5), 963-969.

Cai, H., et al., "A straightforward means of coupling preparative high performance liquid chromatography and mass spectrometry" Rapid Comm. Mass Spectrom. 2002, 16(6), 544-554.

Beavis, R.C., et al., "Off-Line Coupling of a Microbore High-Performance Liquid Chromatograph to a Secondary Ion Time-of-Flight Mass Spectrometer" Anal. Chem., 1990, 62 (13), 1259-1264.

Walker, K.L., et al., "Off-Line Coupling of Capillary Electrophoresis and Matrix-Assisted Laser Desorption/Ionization Time-of-Flight Mass Spectrometry" Anal. Chem., 1995, 67 (22), 4197-4204.

Kassis, C.E., et al., "A Direct Deposition Method for Coupling Matrix-assisted Laser Desorption/Ionization Mass Spectrometry with Gel Permeation Chromatography for Polymer Characterization" Rapid Comm. Mass Spectrom. 1997, 11 (10), 1134-1138.

Preisler, J., et al., "On-Line MALDI-TOF MS Using a Continuous Vacuum Deposition Interface" Anal. Chem., 1998, 70 (24), 5278-5287.

Fei, X., and K. K. Murray, "On-Line Coupling of Gel Permeation Chromatography with MALDI Mass Spectrometry" Anal. Chem., 1996, 68 (20), 3555-3560.

Preisler, J., et al., "Capillary Array Electrophoresis-MALDI Mass Spectrometry Using a Vacuum Deposition Interface" Anal. Chem., 2002 74 (1), 17-25.

Preisler, J., et al., "Capillary Electrophoresis—Matrix-Assisted Laser Desorption/Ionization Time-of-Flight Mass Spectrometry Using a Vacuum Deposition Interface" Anal. Chem., 2000, 72 (20), 4785-4795.

Foret, F., et al., "Subatmospheric electrospray interface for coupling of microcolumn separations with mass spectrometry" Electrophoresis, 2000, 21 (7), 1363-1371.

Murray, Kermit K., "Coupling Matrix-Assisted Laser Desorption/Ionization to Liquid Separations" Mass Spectrom. Rev., 1997, 16(5), 283-299.

Ogorzalek Loo, R.R., et al., "Mass Spectrometry of Proteins directly form Polyacrylamide Gels" Anal. Chem. 1996, 68 (11), 1910-1917.

Gagel, J.J.,and K. Biemann, "Continuous Recording of Reflection—Absorbance Fourier Transform Infrared Spectra of the Effluent of a Microbore Liquid Chromatograph" Anal. Chem., 1986, 58 (11), 2184-2189.

Yang, L., et al., "A New Transport Detector for High-Performance Liquid Chromatography Based on Thermospray Vaporization" Anal. Chem., 1984, 56, 2632-2636.

Miliotis, T., et al., "Capillary liquid chromatography interfaced to matrix-assisted laser desorption/ionization time-of-flight mass spectrometry using an on-line coupled piezoelectric flow-through microdispensor" J. Mass Spectrom. 2000, 35 (3), 369-377.

Hensel, R. R., et al., "Electrospray Sample Preparation for Improved Quantitation in Matrix-assisted Laser Desorption/Ionization Time-of-flight Mass Spectrometry" Rapid Comm. Mass Spectrom., 1997, 11(16), 1785-1793.

Zhan, Q., et al., "A Novel Interface for On-line Coupling of Liquid Capillary Chromatography with Matrix-assisted Laser Desorption/Ionization Detection" Rapid Comm. Mass Spectrom., 1999, 13 (22), 2278-2283.

Abian, J., "The Coupling of Gas and Liquid Chromatography with Mass Spectrometry" J. Mass Spectrom. 1999, 34 (3), 157-168.

Ørsnes, H., et al., "A Rotating Bal Inlet for On-Line MALDI Mass Spectrometry" Anal. Chem., 2000, 72 (1), 251-254.

* cited by examiner

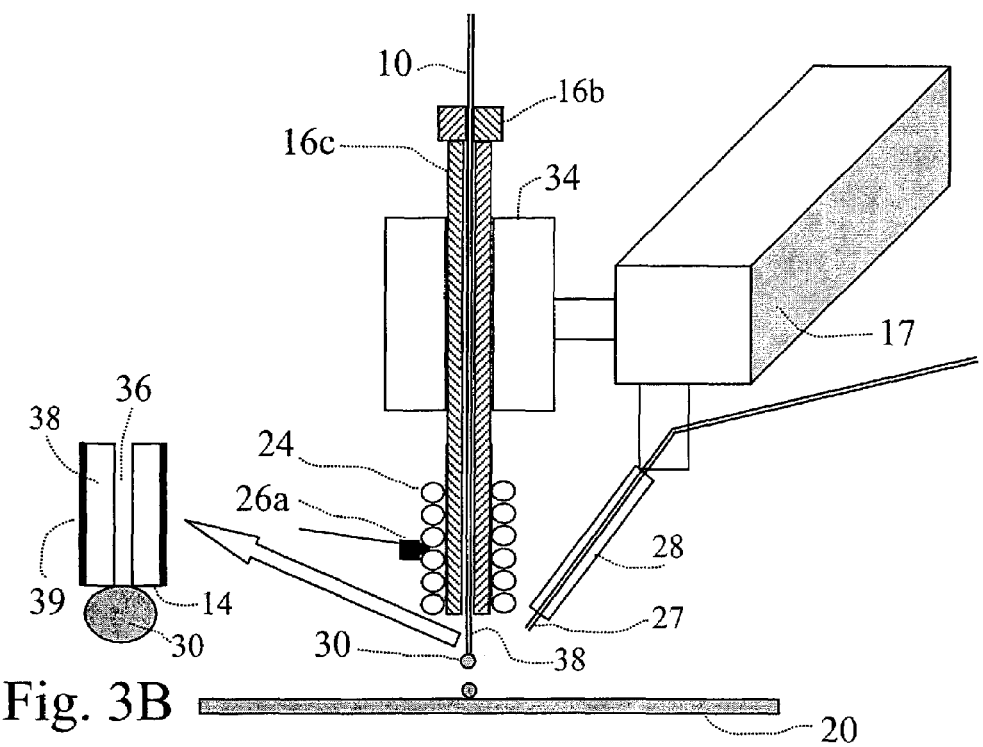
Fig. 3B
Fig. 3A
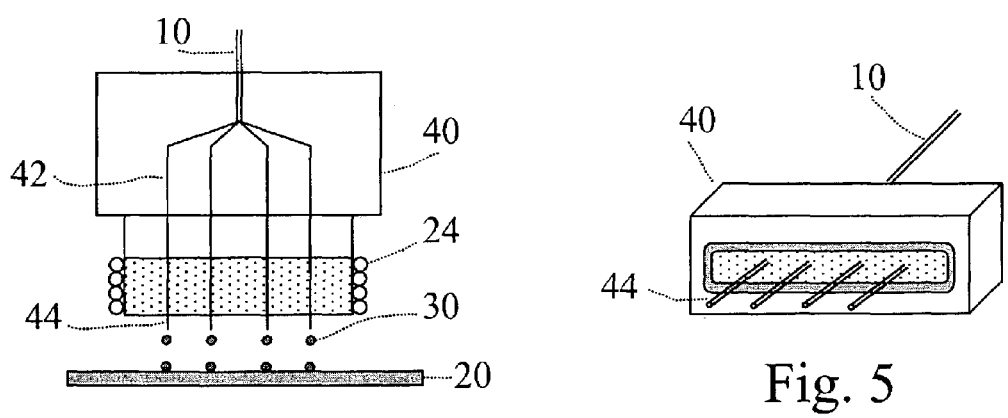
Fig. 4
Fig. 5

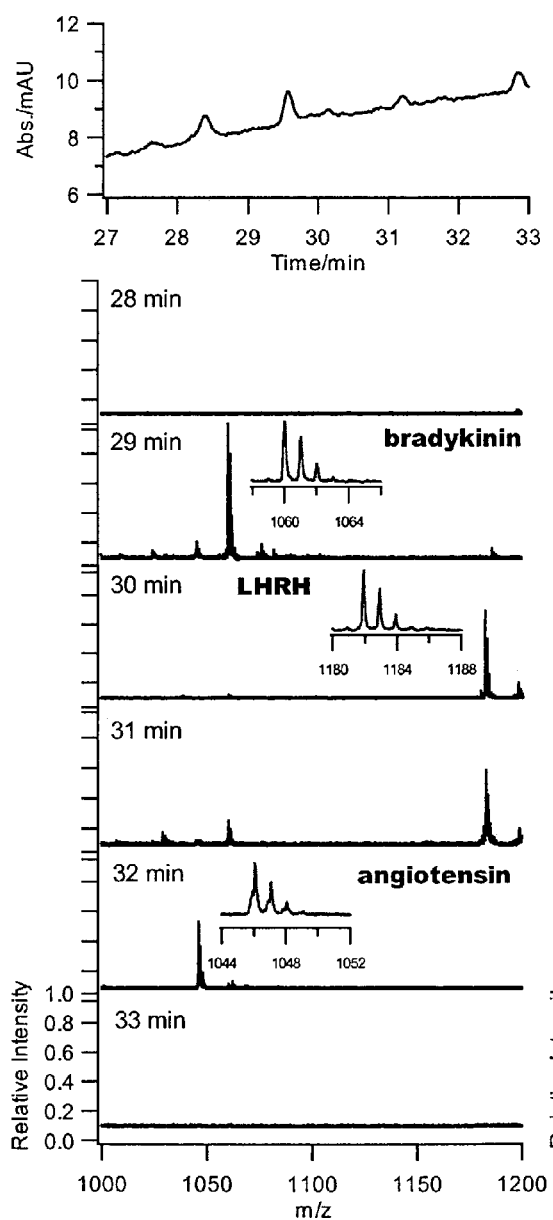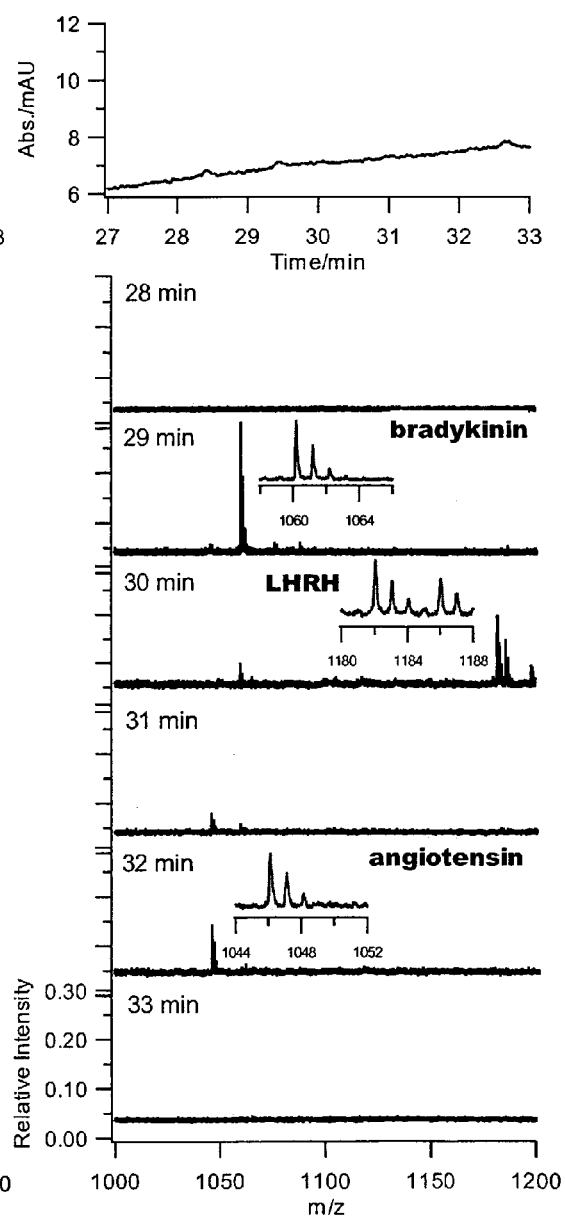
Fig. 6A  Fig. 6C
Fig. 6B  Fig. 6D

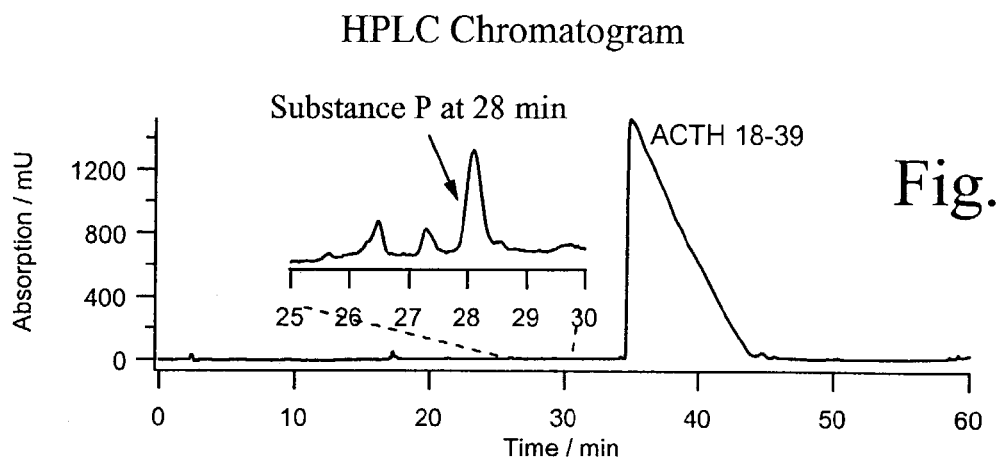
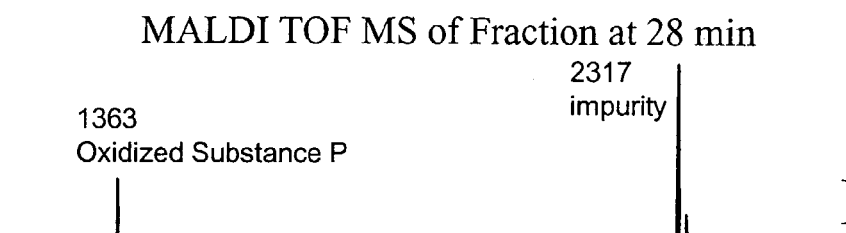

APPARATUS AND METHOD FOR CONCENTRATING AND COLLECTING ANALYTES FROM A FLOWING LIQUID STREAM

FIELD OF THE INTENTION

The invention relates to both apparatus and methods for concentrating and collecting analytes carried in a flowing liquid stream such as the effluent from liquid chromatography (LC) or analyte solution from a flow injection system.

BACKGROUND OF THE INVENTION

Several analytical detectors are available for compound characterization, probing a wide range of physical or chemical properties. Although many detectors possess high selectivity, almost all detectors are responsive to certain interfering compounds, which can either skew, or totally prevent an accurate analysis of the species of interest. In general, due to the presence of multiple analytes in a sample mixture, as well as non-analyte interfering (matrix) components in the sample, a separation step is often required prior to analysis. Therefore, the effective coupling of the separation step to the detection scheme can dictate the ultimate success of the analysis.

Of the many separation platforms available, a widely used method is liquid chromatography (LC). Modern, commercially available LC systems are automated, have high-resolution and separation capacities, are both fast and reproducible, and are based on a variety of distinct separation mechanisms. Owing to their widespread application, many analytical detectors have been modified to couple with LC separations; flow-cell detectors for spectroscopic measurements represent a commonly used example. Many other detectors, such as nuclear magnetic resonance detectors, and mass spectrometry instruments, have also been directly coupled to LC separations.

A potential problem in directly coupling LC separations to analytical detectors lies in the dilution of analytes into the mobile phase (the carrier liquid) of the separation. Since the response of many detectors is concentration sensitive, analyte dilution into the mobile phase results in a loss of detection sensitivity. In addition, the carrier liquid may cause interference in the detector; a minor detector response to the carrier solvent can result in a significant background. Excess liquid solvent has, and continues to be a major concern with direct coupling of LC separations to mass spectrometry (MS) instruments, since these instruments must operate at high vacuum. In addition, if post-separation sample manipulation steps are required, the dilution of sample into carrier liquid may potentially interfere with subsequent workup. For these reasons, it is often necessary to enrich the analyte following a separation.

Analyte concentration or enrichment can be accomplished in one of two general ways: through selective capture or transmission of analytes from the mobile phase, or through selective elimination of the mobile phase. Solvent elimination is most easily achieved by evaporation of the more volatile solvent. Techniques for selected capture or transmission of analytes include molecular weight cutoff filters, dialysis, or capturing analyte onto a solid support. In most cases, these techniques have been demonstrated in an off-line fashion through collection and subsequent manipulation of discrete fractions from the LC separation. Since many fractions can potentially result from a single separation, off-line sample enrichment requires considerable effort. In addition, there is a high risk associated with analyte loss or contamination during the workup process. A method for the enrichment and collection of fractionated analytes in a continuous, automated fashion would allow for a more direct coupling of LC systems to analytical detection schemes, or to subsequent sample workup steps, and would therefore provide a more desirable system.

Several systems have been described in the art that directly incorporate an enrichment of separated components from LC systems for subsequent chemical analysis of the fractionated components. Several of these systems were designed to address the concerns associated with coupling LC to MS instruments. For example, the techniques of thermospray, electrospray, atmospheric pressure chemical ionization, and ionspray are all designed to reduce the solvent being transmitted to the high vacuum region of a mass spectrometer, while allowing the analytes to be transmitted. Similarly, momentum based particle jet separators and membrane separators attempt to selectively transmit analytes to the detector while reducing the amount of solvent (for a review of LC-MS coupling techniques, see for example Abian, J. J. Mass Spectrom. 34, 157-168 (1999)). Although relatively high flow rate couplings can be achieved using the aforementioned devices, the reduction of the solvent comes at the expense of reducing the transmission efficiency of analytes to the detector, with the analyte being spread out over a large spot on the detector or sample plate. Also, these devices are designed for direct coupling to MS instruments; sample collection for subsequent workup or analysis is therefore negated.

In other prior art, systems have been presented that rely on the recovery or collection of analytes from a flowing liquid stream by deposition onto a solid support, or into vials. In doing so, the analyte enrichment and solvent elimination is independent of the detection or subsequent sample workup. The topic of coupling LC separations to MALDI-MS has been reviewed (K. K. Murray, Mass Spectrom. Rev., 1997, 16, 283-299). LC systems have been designed to couple low flow rate separations (<10 µL/min), simplifying a direct coupling to various detectors. U.S. Pat. No. 6,175,112 to Karger et al., discloses a system for the deposition of LC effluent as a continuous track onto a moving sample support. However, such a system suffers from only minimal sample capacity (low flow rate), and consequently, has a lower detection dynamic range.

In order to enrich analytes from higher flow rate separations, various methods for deposition of the eluent onto a solid support have been developed. U.S. Pat. Nos. 4,823,009 and 4,843,243 to Biemann et al., disclose a device for solvent elimination and simultaneous capture of the separated analytes from LC effluent onto a solid, rotating disk. The effluent is heated, and nebulized by a sheath gas flow to achieve rapid evaporation of solvent, depositing the solid analytes on the rotating disk. Dedmezian et al. in U.S. Pat. No. 5,039,614 describe a similar design for coupling LC separation to MS from a solid support in which analytes are deposited on a heated rotating disc by evaporation of the solvent in a subatmospheric pressure environment. The temperature and pressure can be adjusted according to the solvent composition/flow rate. U.S. Pat. No. 4,740,298 to Andresen et al. describes a moving belt interface for coupling LC to MS. This device is also based on similar principles, using a heated nebulizer to deposit samples on a solid support.

Electrospray deposition of the eluent onto a solid support has also been reported, see for example R. C. Beavis, W. Ens, D. E. Main, and K. G. Standing, Anal. Chem. 1990, 62, 1259-1264.

U.S. Pat. No. 5,772,964 to Prevost et al, describes a capillary nozzle for use with liquid chromatographic effluent. An extended portion of the capillary nozzle (20 cm or longer) is directed through a heater which heats the capillary contents to above the boiling point of the solvent in order to evaporate solvent. An upstream nebulizer upstream of the nozzle injects a nebulizer gas into the liquid effluent from the liquid chromatograph. A sheath gas is used at the nozzle outlet to direct the output from the nozzle. This and other designs which use a temperature above the solvent boiling point, particularly when coupled with nebulizing gas, have the disadvantage of producing a conical spray at the nozzle outlet, which forms fine mists and spreads or scatters the analyte out over the collection target. While the use of a sheath gas can provide a concentric focus on the spray which results in smaller deposition spots, analyte loss cannot be prevented due to the difficulty of collecting all fine mists exited from the nozzle on the collection target.

U.S. Patent Application 2002/0092366 to Brock et al, discloses a method and apparatus for depositing liquid droplets from a liquid chromatograph onto a sample plate for mass spectrometry. A capillary nozzle is used to create a liquid droplet and an electric field is generated between the droplet and the plate to polarize the droplet such that it is pulled to the sample plate. This system has the disadvantage that the liquid sample is not concentrated prior to depositing on the sample plate and it can only handle low flow rates.

There remains a need for a device for enrichment of analytes from a flowing liquid stream operating at high flow rates (such as up to 500 µL/min), without the disadvantages of prior systems which use temperatures above the boiling point of the solvent, nebulizers, electric charges or aerosol formation, all of which result in spreading of the analyte. Such a device would be particularly useful as a generally applicable interface for coupling LC to analytical detection schemes such as MS, and particularly MALDI-MS, as well as for collection for subsequent sample workup. Analyte enrichment following LC separation will allow for maximal detection sensitivity and ease of sample workup with minimal analyte loss or contamination. Such a device would also be very useful for concentrating dilute analyte solution without separation such as in a flow injection system where the dilute sample is either continuously pumped to the interface or injected as a sample plug to a flow stream and carried to the interface.

SUMMARY OF THE INVENTION

In one broad aspect, the present invention provides an apparatus for concentrating and collecting one or more analytes in a flowing liquid stream of a carrier solvent composed of one or more solvent components. The apparatus includes a transfer tube which forms one or more aligned bores, each having an inlet and an outlet, the inlet being adapted to accept the flowing liquid stream, and the outlet being adapted to form continuously replaced, hanging droplets of the liquid stream. The apparatus also includes a collection device mounted below the outlet of the transfer tube for collecting the droplets. The apparatus includes a device for heating the liquid stream in the transfer tube to a temperature sufficient to cause partial evaporation of the carrier solvent from the hanging droplets but not exceeding the boiling point of the carrier solvent; and a device for heating the collection device to a temperature sufficient to cause further evaporation of the carrier solvent.

The invention also broadly provides a method for concentrating and collecting one or more analytes in a flowing liquid stream of a carrier solvent composed of one or more solvent components. The method includes the steps of: introducing the liquid stream into a transfer tube which forms a bore having an inlet and an outlet, the inlet being adapted to accept the flowing liquid stream, and the outlet being adapted to form continuously replaced, hanging droplets of the liquid stream; heating the liquid stream in the transfer tube while controlling the temperature of the liquid stream in the transfer tube to a temperature sufficient to cause partial evaporation of the carrier solvent from the hanging droplets without exceeding the boiling point of the carrier solvent; allowing the droplet to dislodge from the outlet of the transfer tube; collecting the droplet on a collection device mounted below the outlet of the transfer tube; and heating the collection device to a temperature sufficient to cause further evaporation of the carrier solvent from the collected droplets.

In a preferred embodiment of the invention, the apparatus and methods are designed for coupling LC separations to detection schemes that involve analysis of the analyte deposited on a solid support. In another preferred embodiment, the system and methods are designed for on-line concentration of analytes, with collection onto a solid support for subsequent sample workup.

Preferred embodiments of the method and apparatus of this invention include one or more of the following features:

- a robotic device adapted for one or more of X, Y and Z motion associated with one or both of the transfer tube and the collection device so as to achieve relative X, X-Y, and X-Y-Z motion (most preferably programmable for motion and the timing of the motion) of the transfer tube and the collection device;
- adjustable temperature heating devices of one or both of the collection device and the transfer tube which allows close control of the extent and rate of evaporation so as to maintain the hanging droplets and avoid solvent and analyte spraying from the outlet of the transfer tube, which thus prevents any significant loss of analyte;
- the collection device being formed from a heat conductive material and formed with a plurality of spaced structures such as wells to confine and retain the collected droplets in a small confined area, such that the analyte is highly concentrated;
- a gas drying device adapted to direct a non-reactive drying gas at one or both of the outlet of the transfer tube and the collection device;
- a device to assist in dislodging the hanging droplets from the outlet of the transfer tube;
- a housing or exhaust system to remove or contain the evaporated carrier solvent; and
- use of an analyte detector to control the timing of the X-Y-Z motion of the robotic device.

Precise control of heating of the flowing liquid as it passes through the heated transfer tube avoids spraying from the outlet of the tube and allows for maximal on-line sample concentration in a hanging droplet. In addition, adjustment of the temperature of the collection device in relation to the temperature of the transfer tube further optimizes analyte enrichment, as well as collection of analyte in small, confined areas on the collection device.

With this system, analytes can be continuously concentrated in an on-line fashion from a flowing liquid stream at flow rates up to 500 µl/min. In addition, by controlling the extent of solvent elimination, analytes can be collected as a dried spot on a solid support, or in a given volume of solvent. The concentrated analytes can be collected as discrete fractions, or as overlapping fractions.

The invention is ideally designed for direct coupling to a liquid chromatograph or a flow injection system. The invention provides an ideal interface for liquid chromatography to mass spectrometry such as with matrix-assisted laser desorption/ionization mass spectrometry (MALDI-MS) and surface-enhanced laser desorption/ionization MS.

BRIEF DESCRIPTION OF THE DRAWINGS

FIG. 3A is a schematic, side sectional view of the heated transfer tube of the present invention, showing an X-Y-Z robotic arm connected to the transfer tube and the drying gas tube.

FIG. 3B is an enlarged view taken from FIG. 3A of the outlet of the transfer tube with a hanging droplet in place.

FIG. 4 is a schematic, side section view of a transfer tube formed from a block having aligned channels formed therethrough for stream splitting.

FIG. 5 is bottom perspective view of the outlets of the stream splitting transfer tube of FIG. 4.

FIG. 6 illustrates results from the use of the method and apparatus of this invention coupled to MALDI-MS for the detection of three peptides (angiotensin II, bradykinin, and LHRH) following HPLC separation and fractionation with a HPLC-MALDI interface according to Example 2, in which:

FIG. 6A shows the UV trace of the separation, from 27 to 33 min. following injection, using an injection amount of 20 μl of the peptide mix containing 1 pg/μl of each peptide (about 1 fmol/μl);

FIG. 6B shows the resulting MALDI spectra from fractions collected over the same time interval;

FIG. 6C shows the UV trace from the injection of 5 μl of the peptide mix containing 1 pg/μl of each peptide (about 1 fmol/μl); and FIG. 6D is the corresponding MALDI spectra from analysis of the corresponding fractions.

FIG. 7 illustrates results of direct MALDI from analysis of substance P in Example 3 in the presence of an excess amount of ACTH 18-39, in which:

FIG. 8 illustrates comparative results from the use of the method and apparatus of this invention operating as the HPLC-MALDI interface following separation of substance P in the presence of varying amounts of excess ACTH 18-39, on a 1 mm $C_{18}$ column according to Example 3, in which:

FIG. 8A shows the UV trace recorded for the separation of substance P and ACTH (1000:1 mole ratio of ACTH to substance P, 5 μg total injected);

FIG. 8B is from the analysis of a 1000:1 mole ratio of ACTH 18-39 to substance P, 2 pmol substance P injected;

FIG. 8C is from the analysis of the $10^4$:1 mole ratio, 203 fmol substance P injected;

FIG. 8D is from the analysis of the $10^5$:1 mole ratio, 20 fmol substance P injected; and FIG. 8E is from the analysis of the $10^6$:1 mole ratio of ACTH to substance P, with 2 fmol substance P injected.

FIG. 9 illustrates the analysis of whole proteins using the method and apparatus of this invention with MALDI MS following separation of a 7-protein mixture and collection with an HPLC-MALDI interface, in accordance with Example 4, in which:

FIG. 10 illustrates further results using the method and apparatus of this invention according to Example 6, in which:

DETAILED DESCRIPTION OF THE PREFERRED EMBODIMENTS

An apparatus, along with methods, has been developed that allows for the enrichment, i.e., concentration, of analytes, from a flowing liquid stream, and collection of said components for off-line analysis or subsequent sample workup. One of the major advantages of this system is that analytes are initially concentrated on-line from the hanging droplets, in a near wall-less environment, resulting in a lower risk of analyte loss due to adsorption to container walls. Another important advantage is that the collected analytes are captured in a small confined surface area on the collection device, thus maximizing unit area concentration, as well as spatial resolution, and minimizing the analyte adsorption to the surface. The apparatus is designed to handle liquid flow rates ranging from sub-microliter per minute flows, up to on the order of 500 μL/min. The ability to concentrate and fractionate analytes from high flow rate LC systems allows for larger amounts of analytes to be enriched, fractionated and collected for subsequent analysis or manipulation. As a result, the system has a high concentration dynamic range.

The apparatus and method of this invention are illustrated in the figures and described herein in a preferred embodiment designed for collection of effluent from LC separations operating at low to mid-range flow rates, approximately between about 10 and 500 μl/min, onto a collection device for further offline analysis or subsequent sample workup. The invention has broad application to the concentration and collection of analytes moving in or through a continuous or near continuous liquid stream (a carrier solvent composed of one or more solvent components) operating at similar flow rates. The apparatus can also accommodate lower flow rate systems (<10 μl/min), down to sub-microliter per minute flow rates.

Figure 1:
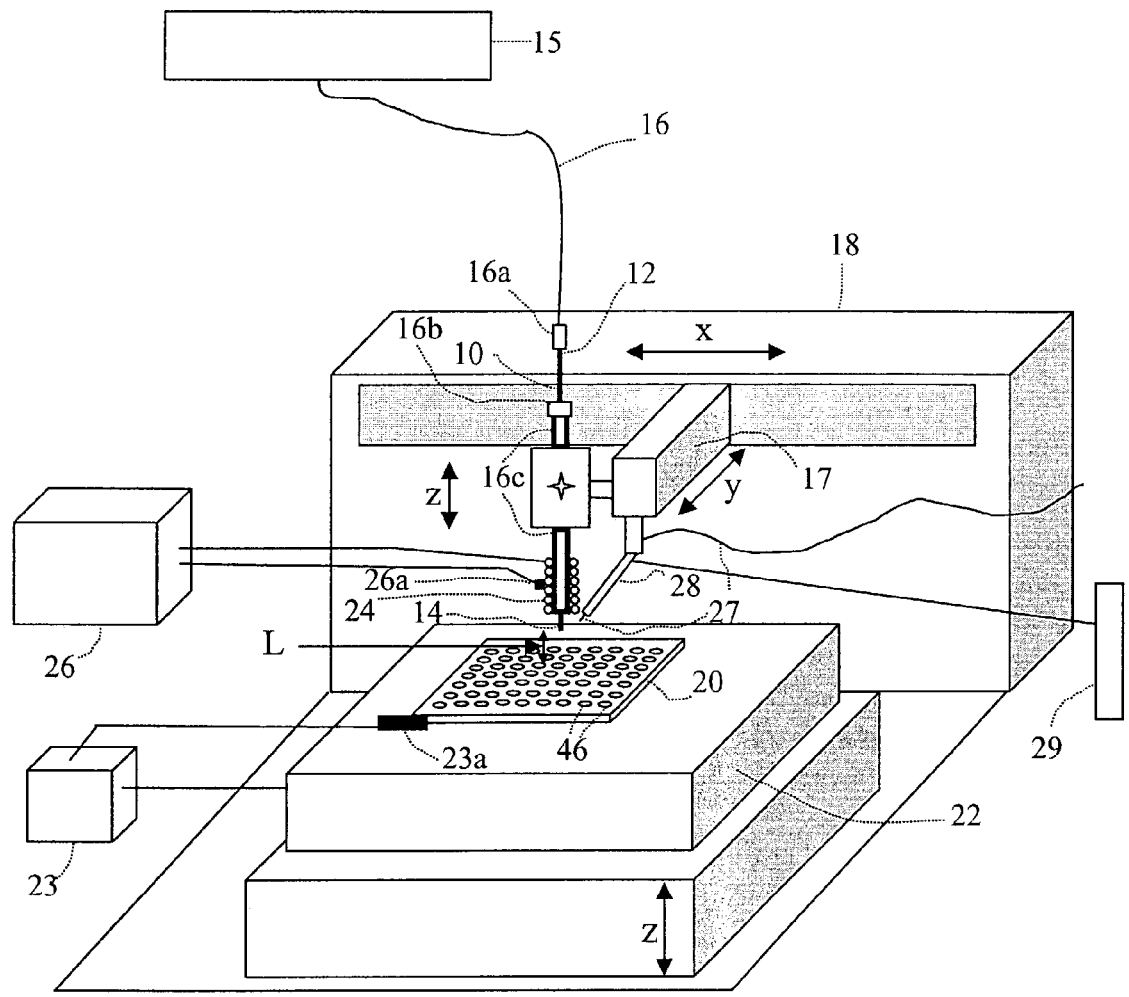
FIG. 1 shows a schematic perspective view of the apparatus of this invention.

FIG. 1 shows one preferred embodiment of the on-line concentrator, fractionation and deposition apparatus of this invention. The apparatus includes a transfer tube 10 having an inlet end 12 and an outlet end 14. The inlet 12 is easily adapted to receive the effluent from an external flow stream delivery system 15, such as a high pressure liquid chromatograph (HPLC) or a flow injection system. In FIG. 1, the inlet 12 is shown to be connected to receive an LC effluent flowing through chromatography tubing 16, a union 16a and a fitting 16b. It is possible to use the LC tubing 16 itself as the transfer tube, however in FIG. 1, the transfer tube 10 is shown held within a supporting tubing 16c, which holds the transfer tube 10 in a vertical position. The transfer tube 10 is mounted vertically onto a robotic arm 17 of a movable x-y-z stage 18, allowing the effluent to be precisely positioned with x-y-z coordinates. A collection device 20 is located below the outlet 14 of the transfer tube 10. Suitable x-y-z stages are well known in fraction collectors, and are generally computer programmable to control the x-y-z motion and the timing of that motion. One exemplary fraction collector device which may be used is a microcomputer controlled Advantec SF-2120 super fraction collector (Advantec MFS, Inc., Duplin, Calif.). In a preferred embodiment, the movement and positioning of the x-y-z stage can be programmed by the user. In another preferred embodiment, the timing for movement of the x-y-z stage is predetermined by the user. In another preferred embodiment, the timing of movement of the x-y-z stage can be controlled by a feedback response from a microprocessor, for example in response to a detector (not shown) which monitors the flowing liquid stream and detects analytes carried in this liquid stream, as is known in the art.

The position of the transfer tube outlet 14 relative to the collection device 20 is controlled by programming the fraction collector to move the robotic arm 17, and therefore the attached transfer tube 10, to a defined position for a given time interval. In this manner, fractions are collected at predetermined time intervals, as, for example, in one minute time intervals. Alternatively, the time interval for fraction deposition is based on the response of an on-line detector signal, such as from a UV detector (not shown), monitoring the LC effluent. Other detector outputs may be used, for example a fluorescence signal, a conductivity measurement, or a change in refractive index of the liquid stream.

The outlet end 14 of the transfer tube 10 is positioned directly above the collection device 20, spaced by a vertical distance, shown as L in FIG. 1. The distance L can be adjusted by positioning the transfer tube 10 relative to the collection device 20, or by moving the collection device 20 up or down relative to the transfer tube. In a preferred embodiment, the vertical distance L is controlled with the movable x-y-z stage 18 of a fraction collector, however, the collection device 10 might in addition or alternatively include a movable Z component of movement, as indicated schematically in FIG. 1.

Both the transfer tube 10 and the collection device 20 are heated by heating devices described below, in a controlled manner in order to evaporate the carrier solvent without spraying, ionizing, nebulizing, splattering or uncontrolled boiling of the carrier solvent, all of which cause an undesired spreading or loss of the sample analyte on the collection device 20.

The collection device 20 is preferably mounted horizontally on a heating block 22, equipped with adjustable temperature controllers 23, such that the collection device 20 is heated to evaporate the carrier solvent as the droplets land on the plate. A suitable heating block for use with the apparatus is the Boekel Scientific Model 11001 dry bath heating block incubator. A temperature sensor 23a is included on a side of the collection device 20 to monitor its temperature. The collection device 20 is preferably formed from a heat conductive material.

The contents of the transfer tube 10 are heated with a heating coil 24 wrapped around a vertical portion of the supporting tubing 16c. The coil 24 is connected to an adjustable temperature controller 26. The temperature of the transfer tube 10 is monitored with a temperature sensor 26a. The temperature controller 26 may be a variable autotransformer (potentiostat). A suitable temperature controller for use is a Barnant Model 689-0010 temperature controller (Barrington, Ill., U.S.A.) equipped with a thermocouple sensor 26a for monitoring the temperature of the heating coil. The temperature sensor 26a is placed midway of the heating coil 24. Alternatively, the heating device may be a heating block that either partially or completely surrounds the transfer tube 10. The heating device might also utilize electromagnetic radiation that is directed at the liquid flowing through the transfer tube 10. Examples include UV, IR or microwave radiation. In the case of electromagnetic radiation being used, the transfer tube 10 and/or the supporting tubing 16c is formed of a material which allows for efficient transfer of the electromagnetic radiation to the liquid flowing inside the transfer tube 10. In general, the heated portion of the transfer tube 10 need be no more than about 1 to 10 cm in length. Alternate heating devices may also be used for the block heater 24 used to heat the collection device 20.

To further assist in the evaporation of the carrier solvent, a gas drying device may be used. As shown in FIG. 1, a stream of non-reactive gas such as nitrogen gas is flowed through a drying gas line 27 directed at the outlet 14 of the transfer tube 10. Alternatively, or in addition, the drying gas may be directed at the collection device 20. The gas drying line 27 is preferably heated, for example with a heating coil 28 wrapped around the line 27 and connected to an adjustable temperature control 29. As shown in FIG. 1, the gas drying line 27 is preferably mounted to the robotic arm 17, such that it is moved with the transfer tube 10.

FIGS. 3A, 3B, 4 and 5 show exemplary details of preferred embodiments of the transfer tube 10. The transfer tube 10, including its dimensions and outlet configuration, is designed to ensure that the flowing liquid stream moving therethrough forms continuously replaced hanging droplets 30 at the outlet 14, in a manner such that controlled heating of the flowing liquid results in evaporation of the solvent from the hanging droplet 30, and not within the transfer tube 10 itself In FIG. 3A, the transfer tube 10 is shown held vertically within the supporting tubing 16c, in a mounting block or tube 34. The mounting block 34 is connected to a robotic arm 17 for x-y-z motion, as set out above. The transfer tube 10 may be formed from silica capillary tubing, with a small capillary bore 36 having a preferred inner diameter of about 5 to 500 μm, more preferably about 50 to 200 μm, and having a preferred outer diameter of 75 to 1000 μm. The supporting tubing 16c may be formed from a stainless steel tube sized to accommodate the transfer tube

10. For example a 0.159 cm (¹⁄₁₆th inch) outer diameter stainless steel tube with an inner diameter of 250 μm may serve as a supporting tubing 16c to hold a transfer tube having an inner diameter of 50 μm and an outer diameter of 185 μm. The transfer tube 10 is fitted inside the supporting tubing 16c by using the fitting 16b.

As shown in FIG. 3A, the transfer tube 10 extends beyond the heated portion of the supporting tubing 16c, forming an extension line 38, by a distance preferably ranging from 0.1 to 1 cm, in order to allow for hanging droplets 30 to form at the outlet 14 of the transfer tube 10.

As best seen in FIG. 3B, the transfer tube 10 may be formed from a material, or include a surface coating 39, to decrease the surface tension of the hanging droplets 30 and to prevent the hanging droplets 30 from creeping around the outlet 14 of the transfer tube 10 (creeping can result in the formation of a very large droplet). This surface coating might only be used along the outer wall at the outlet 14, although many commercial tubings are precoated along their entire length, inside and/or outside, with such coatings. Such coatings might also add the benefit of increased mechanical strength. Examples of surface coated or modified capillary tubing are silica capillaries with polyimide coatings, for instance available from Polymicro Technologies (Phoenix, Ariz.), and silica tubing treated with siliconizing agent Glassclad-18™ (United Chemical Technologies, Bristol, Pa.).

Another preferred embodiment of the transfer tube 10 is shown in FIGS. 4 and 5. Chromatography tubing 16 carrying the flowing liquid stream is interfaced to the transfer tube 10 in the form of a line splitter 40. The line splitter 40 is formed with a plurality of vertically aligned channels 42, each having a small capillary bore, as described above. A vertical portion of the line splitter 40 is heated by a heating coil 24, as described above. Each of the channels 42 terminates in an extension line 44, as best shown in FIG. 5, which extends below the heated portion of the line splitter 40. The outlet end of each extension line is capable of forming and supporting a hanging droplet 30. The spacing between the extension lines 44 is preferably set as close as possible without allowing for the several hanging droplets 30 to fuse. The droplets from this line splitter 40 are collected in a single fraction or separated fractions on the collection device 20. This style of transfer tube 10 is particularly suited for collection of droplets into a multiwell microtitre plate. Thus, the four extension lines 44 shown in FIG. 5 may be spaced such that their collective output is received into a single well with a diameter of less than 1 cm, in for example a standard 96 well microtiter plate.

The use of the line splitter 40 increases the solvent evaporation rate from the droplets due to an increase in the surface to volume ratio of the droplets. Without being bound by theory, it is believed that the rate of solvent evaporation from a droplet is related to the surface area of the droplet. A higher surface to volume ratio can be achieved by forming several smaller droplets rather than one large droplet, thus increasing the evaporation rate. The number of hanging droplets, i.e., the number of extension lines 44 and channels 42, can therefore be optimized according to the overall flow rate of the system.

The temperature of the flowing liquid through the transfer tube 10 is carefully controlled. This temperature can be optimized according to several parameters, including the solvent composition of the flowing liquid, as well as its flow rate. Preferably, the temperature of the flowing liquid is adjusted to just below its boiling point, in order to prevent the formation of gas vapor bubbles inside the transfer line.

As the heated liquid exits the transfer tube, it forms a hanging droplet that clings to the end of the transfer tube outlet 14 by virtue of surface tension. The overall rate of growth of the droplet is controlled by two differential parameters: (1) the rate at which material is added to the droplet, and (2) the rate at which material is evaporated from the droplet. The rate at which material adds to the droplet is determined by the volume flow rate of the liquid that is continuously flowing from the transfer tube 10. Under optimal conditions, and depending on the volume flow rate, solvent evaporation from the hanging droplet can eliminate of up to 90% of the total solvent flowing into the droplet. The hanging droplet thus acts as a near wall-less container for concentration of analytes. Since the rate of material going into the droplet is higher than the rate of solvent evaporation, the droplet will grow in volume until a critical size is reached, at which point gravity overcomes the surface tension holding the droplet. At this point, the bulk of the hanging droplet falls off the end of the transfer tube 10 and is collected on the collection device 20 directly below the outlet 14.

The apparatus may include a device for dislodging the hanging droplets at defined time intervals. In doing so, the precise time of collection of the fraction is well controlled. In addition a smaller droplet, having a higher surface to volume ratio, experiences more efficient solvent evaporation. By preventing the droplet from growing too large, maximal concentration efficiency is achieved. The device for dislodging the droplets may use a pulsed gas, whether it be a sheath gas, or the drying gas shown in FIGS. 1 and 3A. Alternatively, the device may dislodge the droplets piezo-electrically, electrically, ultrasonically, or magnetically. In yet another embodiment, a touchdown technique may be used, for instance, the z motion of the collection device 20 may be used to allow for blotting or touchdown, that is the droplet 30 may be removed from the end of the transfer tube 10 by raising the collection device 20 to the outlet 14 of the transfer tube, and allowing the droplet to touch the collection device 20. This embodiment is shown schematically in FIG. 1 with the z-component movement of the collection device 20.

Figure 2A:
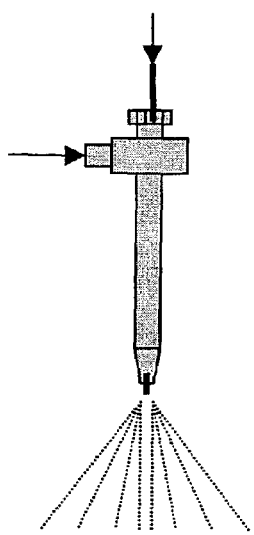
FIG. 2A shows a schematic side view of a prior art nebulizer, which delivers a conical spray.
Figure 2B:
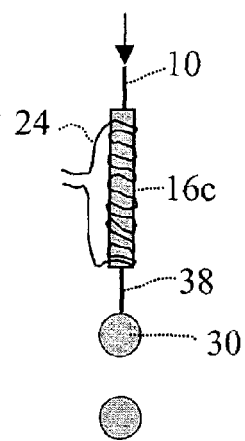
FIG. 2B is a schematic side view of the transfer tube of the present invention delivering droplets that are too large for optimal solvent evaporation from the hanging droplet, resulting when the temperature of the flowing liquid stream in the transfer tube is too low.
Figure 2C:
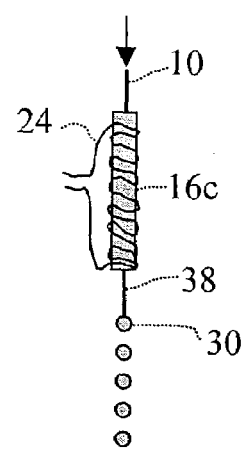
FIG. 2C is a schematic side view of the transfer tube of the present invention delivering continuously replaced, hanging droplets of the liquid stream that result when the temperature of the flowing liquid stream is appropriately adjusted.
Figure 2D:
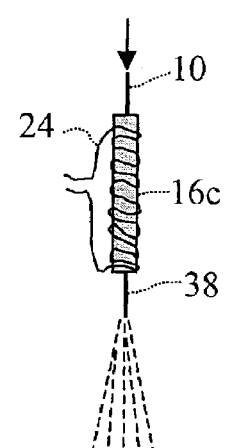
FIG. 2D is a schematic side view of the transfer tube of the present invention delivering a conical spray of droplets, as opposed to continuously replaced hanging droplets, resulting when the temperature of the flowing liquid stream exceeds the boiling point of the carrier solvent.

The collection of relatively large droplets, as opposed to a nebulized spray of prior art, allows for fractionation of the effluent into small, well-defined areas. By collecting the analyte in the smallest possible area on the collection surface, the unit surface area concentration of the deposited sample spot is maximized. Analyte loss due to surface adsorption on the collection device is also minimized. In addition, smaller spot size means that sample fractions can be collected in close proximity in an array format. This allows for an increased number of fractions to be collected on a given size collection surface.

The optimization of the hanging droplet formation and solvent evaporation is principally through temperature control of the contents of the transfer tube 10. In addition, the use of the drying gas and/or the droplet dislodging device assist in solvent evaporation, as well as in dislodging the hanging droplets. This optimization is illustrated in FIG. 2. FIG. 2A shows the undesired conical spray of a nebulizer nozzle such as a typical prior art thermospray type nebulizer. Collection of sample from this type of nebulizer results in large deposited sample spots and scattering, thus lowering the unit area surface concentration of analyte on the collection device and resulting in analyte loss during the collection process.

The operation of the apparatus of the present invention is shown in FIGS. 2B-2D at various temperatures. FIG. 2B depicts operation when the temperature of the transfer tube 10 is set too low. Under these operating conditions, insufficient solvent evaporation from the hanging droplet 30 and high surface tension due to lower temperature of the transfer tube 10 results in the formation of large droplets, which fall from the transfer tube 10 and are collected onto the collection device 20 below. As a result, only minimal on-line enrichment of analytes is achieved. Also, the large droplets landing on the surface of the collection device 10 at a higher rate result in the formation of larger spot sizes, meaning low unit surface area concentration. In FIG. 2C, the temperature of the transfer tube 10 is raised to optimal levels, close to but below the boiling point of the carrier solvent. Under these conditions, solvent evaporation from the hanging droplets 30 maintains smaller droplet size and the surface tension is reduced so that it can be overcome by a smaller size of droplet. An optimal droplet size is about 50 to 500 nl volume per drop, as collected on the collection device 20. In FIG. 2D, the operation at temperatures above optimal temperature levels is depicted. Under these conditions, boiling (vaporization) of the LC effluent either inside the transfer tube 10 or immediately after exiting results in the nebulization of LC effluent. As previously described with the thermospray effluent of FIG. 2A, this nebulization results in spreading out the area of sample as it exits the transfer tube 10. As a result, the cross-sectional area of the collected sample increases, thus lowering the unit surface area concentration of the collected analytes on the collection target.

An important variable in the operation of the concentrator apparatus is in controlling the relative temperature of the collection device, in relation to the temperature of the contents of the transfer tube 10. A large difference in temperature between the collection device 20 and the droplet results in solvent vapor bubbles forming at the base of the collected droplets as the droplet is further heated the collection device 20. These trapped vapor bubbles rapidly expand as the droplet is heated, causing splattering of the droplet, which results in undesired spreading of the sample, reducing the surface concentration, as well as increasing cross contamination between spots on the collection device. In general, larger droplets, and droplets at lower temperatures more easily form and trap vapor bubbles, increasing the risk of splattering on the collection device. Thus, optimizing the transfer tube parameters to allow for the small droplets that are already heated to near the solvent boiling point prior to being collected on the collection device will reduce the likelihood of droplet splattering, and thus increase the overall solvent elimination efficiency. By adjusting the temperature of the collection device 20 relative to the transfer tube 10, efficient solvent evaporation can continue on the collection surface, without the formation of trapped vapor bubbles that lead to splattering. Preferably, the temperature of the flowing liquid in the transfer tube 10 is kept below, but near the boiling point of the carrier solvent. An optimal temperature of the transfer tube 10 can be determined by first determining a threshold temperature at which a spray of fine mist is formed at the exit of the transfer tube 10. The temperature of the transfer tube 10 can then be reduced to within about 10° C. below the threshold temperature so that the hanging droplets are formed at the exit of the transfer tube 10. Preferably, the temperature at the collection device is maintained at a temperature which is at or above the boiling point of the least volatile component of the carrier solvent.

The collection device 20 used for deposition of samples can be of many different forms, such as a multiwell microtiter plate or a target for laser desorption ionization target formed with a plurality of wells having openings sized between about 0.2 and 5 mm in diameter. In a preferred embodiment, the collection device is a flat, solid support that may be composed of metal, glass, or polymeric material. A heat conductive material is preferred. The collection device may be formed from or use a coating of a material which reduces analyte adsorption. As is known in the art, predefined structures such as wells, dimples, coated spots which attract the sample, or moated structures may be used to assist in collecting and confining analytes within the droplet on the collection device 20. For laser desorption ionization targets, samples are collected in the form of dried sample spots, resulting from complete solvent evaporation. The droplets or dried sample spots are collected in discrete spots that are arranged in an array format. The collection device 20 can act as the sample holder for various analytical detection devices, such as a mass spectrometer or a Fourier Transform Infrared (FTIR) spectrometer or a fluorescence spectrophotometer. In a particularly preferred embodiment, the collection device is a standard target used in commercial MALDI-MS instruments, such as the 96 sample spot MALDI target from Applied Biosystems (Boston, Mass., U.S.A.). The dried sample spots can be analyzed by MALDI-MS by adding matrix solution directly on top of the dried sample spots. In another embodiment, the matrix is pre-coated to the MALDI target. During the collection process, the hanging droplet lands to the matrix particles on the target, partially or fully dissolves the matrix, and then dries to form matrix and analyte co-crystals for MALDI-MS analysis.

In another embodiment, the collection device 20 is a flat, solid metal support containing small wells 46 arranged in an array (as shown in FIG. 1). The wells 46 further aid in confinement of the collected analytes, allowing for the higher possible unit area concentration. These wells may contain a functionally active surface at the bottom of the well, such as a material used to capture or retain analytes as they contact the surface. The movable robotic arm 17 at the x-y-z stage 18 controls the position and motion of the transfer tube 10 such that the concentrated effluent is deposited inside the wells 46. This collection device 20 can also act as a target for mass spectrometric analysis, such as in MALDI-MS.

In anther embodiment, the collection device 20 is a microtiter plate. This could be, for example, a 96 well format or a 384 well format. In this case, the movable robotic arm 17 at the x-y-z stage 18 controls the transfer tube 10 positioning such that analytes are collected in discrete wells of the microtiter plate. In another embodiment, the collection device 20 contains a derivatized surface for capturing specific components as it is concentrated and fractionated by the on-line concentrator. For example, this surface could be a bonded phase silica surface (C18 surface) for capture of components. The surface could also contain immobilized binding ligands for selected capture of specific components. The derivatized surface can be any type to allow for capture of some or all components from the LC or flow injection effluent.

The system provides for on-line concentration through solvent evaporation in a near wall-less environment and therefore results in the collection of separated analytes with minimal sample loss. Maximal concentration of the fractionated analytes is achieved by collecting the droplets in small spot sizes, thus providing high unit surface area concentrations. The performance of the invention is illustrated in the non-limiting examples below, highlighting its ability to enrich analytes from LC effluent operating at high flow rates. The examples demonstrate the particular utility of the present invention for the collection and concentration of large biological or chemical samples, such as oligopeptides, oligonucleotides, lipids, glycoproteins, polysaccharides and carbohydrates.

EXAMPLES

The following are a set of experiments performed using a particular embodiment of the apparatus of this invention as an on-line concentrator and fraction collection device in an HPLC-MALDI-MS interface, similar to that set out in FIG. 1. The collection device consisted of either a MALDI target for off-line mass spectrometric analysis of the fractionated components, or a 96-well microtiter plate. Using the MALDI target, the apparatus of this invention acted as an LC-MALDI interface. In the examples, protein or peptide samples were separated on various reversed-phase liquid chromatography (RP-HPLC) columns operating at various flow rates.

Materials and Methods:

The transfer tube was constructed by placing a silica capillary (outer diameter 180 μm, inner diameter 50 μm) having a polyimide coating (Polymicro Technologies) inside of a stainless steel tube, with dimensions of 0.156 cm outer diameter and 250 μm inner diameter, and 12 cm in length. The capillary extended beyond the outlet of the stainless steel tubing for a distance of 7 mm. In order to supply heat to the stainless steel tubing, a wire heating coil (0.75 mm diameter) was wrapped around the tube over a distance of 2.6 cm, having a total of 20 coils around the stainless steel tube. This transfer tube was positioned in the x-y-z stage of a fraction collector as shown in FIG. 1, with a spacing of 0.4 cm between the outlet of the transfer tube and the collection device.

Reversed-phase HPLC separations were performed on an Agilent 1100 series HPLC pump (Agilent, Palo Alto, Calif., U.S.A). The columns used for separation were VYDAC™ bonded phase silica columns ($C_{-8}$ or $C_{18}$ columns) of various dimensions. The solvent system used to perform the separations consisted of water containing 0.1% v/v TFA (trifluoroacetic acid), (solvent A), and acetonitrile with 0.1% v/v TFA (solvent B). A solvent gradient was used over the course of the separation, in which the percentage of solvent B was increased over the duration of the run. Samples were collected on two types of MALDI targets. The first MALDI target was a commercially available MALDI target (Applied Biosystems, Boston, Mass.) that was gold coated, having a 10×10 arrangement of wells that are approximately 2.4 mm in diameter, and ~0.1 mm in depth. The second target was a custom built plate composed of 0.159 cm (1/16") thick stainless steel, with dimensions of 57.4×56.9 mm, again having a 10×10 arrangement of wells, with diameters of 0.8 mm and a depth of ~0.1 mm. MALDI-MS analysis of the deposited sample fractions was performed using α-cyano-4-hydroxy cinnamic acid (HCCA) as matrix. The matrix solution was prepared by saturating HCCA in 40% acetonitrile in water containing 0.5% v/v TFA. MALDI sample preparation consisted of adding 0.6 μl of the matrix solution on top of the dried sample spots and allowing the solvent to evaporate to complete dryness at room temperature. Samples were analyzed on a Bruker Reflex III time-of-flight mass spectrometer (Leipzig, Germany) or a MDS Sciex hybrid quadrupole time-of-flight mass spectrometer (Concord, Canada). Identification of proteins from MS data was accomplished using the MASCOT software program, available on the internet at the Matrix Science Ltd. website (matrixscience.com). All figures represent unsmoothed experimental data.

Example 1

The HPLC-MALDI Interface

The extent of heat applied to the transfer tube is adjusted according to the solvent composition of the flow stream and flow rate. An example of temperature settings for the transfer tube is shown below. This experiment was done with a fixed flow rate of 40 μl/min and there was no nitrogen drying gas directed to the hanging droplets. At the carrier solvent composition of 10% acetonitrile and 90% water, the optimal heating coil temperature determined from the thermocouple sensor placed at the midway of the coil (FIG. 3A) was 270° C. The droplet temperature was measured by placing a thermocouple sensor below the transfer tube exit and, when the droplet lands to the sensor a temperature reading was recorded. The average droplet temperature was found to be 52° C. To determine the volume of effluent after the carrier solvent has been evaporated in the interface, the droplets were collected in a vial for 10 min and the solution volume was then measured. It was found that the effluent volume was 120 μl or the effluent flow rate of 12 μl/min, which is much lower than the initial flow rate of 40 μl/min. This result indicates that a large fraction of the carrier solvent was eliminated from the droplet interface. The droplet-dropping rate was about 0.5 Hz. As the acetonitrile content in the carrier solvent increases, the optimal temperature of the transfer tube is decreased. When a carrier solvent of 50% acetonitrile and 50% water was used, the optimal heating coil temperature was set at 245° C. The average droplet temperature was found to be 50° C. The effluent flow rate after the interface was 8 μl/min. The droplet-dropping rate was about 0.3 Hz. When a carrier solvent of 90% acetonitrile and 10% water was used, the optimal heating coil temperature was 240° C. The average droplet temperature was 46° C. The effluent flow rate after the interface was 4 μl/min. The droplet-dropping rate was about 0.2 Hz. During the HPLC experiment with varying compositions of carrier solvent over a predetermined duration of separation, the temperature of the heating coil can be programmed to follow the changes of the solvent compositions in order to maximize solvent evaporation from the hanging droplets without the formation of a spray of fine mists.

The interface used incorporated a block heater to impart heat to the MALDI target plate. The target was initially heated to 120° C. for starting solvent conditions in a typical HPLC separation of peptides and proteins (2% acetonitrile), and then was gradually adjusted down to 110° C. as the percentage of acentonitrile increased to 90%. The boiling and splattering points of different percentage of water/acetonitrile solvent mixtures on a MALDI target were investigated. It was found that droplets of pure water would boil and splatter on the MALDI target plate at plate temperatures above 125° C. A 50% acetonitrile/water droplet of the same volume boiled at approximately 115° C., whereas a droplet of pure acetonitrile boiled on the plate at 90° C. These boiling and splattering points are dependent on the droplet size, as well as the starting temperature of the droplet. Larger droplets, as well as droplets that were initially at lower temperatures more easily trapped air bubbles, and therefore splattered during the solvent evaporation process. By heating the LC effluent in the transfer tube, the effluent exited the transfer tube at an elevated temperature. In addition, smaller droplets (about 50-500 nl) fell on the heated MALDI plate. The combination of these two factors, allowed for more efficient solvent elimination without solvent splattering, and resulted in the collection of smaller sample spots.

During the spotting process, a stream of hot $N_2$ gas (100° C.) was directed at the outlet end of the transfer tube and the MALDI target, which further reduced droplet size and aided in solvent elimination. Under the above conditions, the LC effluent could be confined to the 0.8 mm diameter wells of the custom-built MALDI target at flow rates of 5-50 µl/min, with 1 min collection time per well. At flow rates up to 200 µl/min, 1 min fractions could be confined to the 2.4 mm diameter wells of the commercial MALDI target from Applied Biosystems.

This example illustrates some of the optimal temperature settings of the transfer tube and of the collection device, to achieve maximal solvent elimination without boiling in the transfer tube or splattering on the collection device.

Example 2

Detection Sensitivity of Peptides by Off-Line MALDI-MS

The detection sensitivity of the HPLC-MALDI interface was demonstrated from the analysis of a dilute peptide mixture. The standard peptide mixture contained 1 ng/µl of each of the following: human angiotensin II, bradykinin, and Luteinizing Hormone-Releasing Hormone (LHRH) was diluted 1000 times with MilliQ water to a dilute peptide mixture contained 1 pg/µl of each peptide (about 1 fmol/µl). Either 20 µl, or 5 µl of said peptide mixture was subjected to RP-HPLC separation on a 0.3 mm I.D. $C_8$ RP-HPLC column at a flow rate of 6 µl/min. The effluent was monitored by the integrated UV detector (214 nm) of the Agilent 1100 HPLC system. The effluent was then interfaced to the transfer tube and collected on the custom-built stainless steel target in 1-min fractions. FIG. 6A displays the UV trace between 27 min to 33 mm following injection of a 20-µl peptide mixture, and FIG. 6C is the corresponding UV trace at the same time interval when 5 µl were injected. The MALDI-MS spectra obtained from the analysis of the fractions collected at these time intervals are shown in FIGS. 6B and 6D for the respective 20 µl and 5 µl sample injection. Note, for example, that the MALDI spectra corresponding to 28 min refers to the effluent collected between 27 and 28 min. It can be seen from FIG. 6A that distinct UV signals can be seen for each of the three peptides at 20 µl injection (~20 fmol per peptide), however the UV signals decreased below the detection limit when 5 µl (~5 fmol) was injected (FIG. 6C). The corresponding MALDI-MS spectra (FIGS. 6B and 6D), however, display strong signals for all three peptides, even at the 5 fmol level. In fact, MALDI signals were still observed for these peptides at the 1-fmol level (spectra not shown). This level corresponds to the detection limit that is observed when these peptides are individually subject to direct MALDI analysis (i.e., without HPLC separation). This example thus illustrates that the apparatus of this invention, functioning as an HLPC-MALDI-MS interface, does not cause analyte loss.

Example 3

Dynamic Range Test

Figures 7A, 7B, 7C, 7D, 7E:
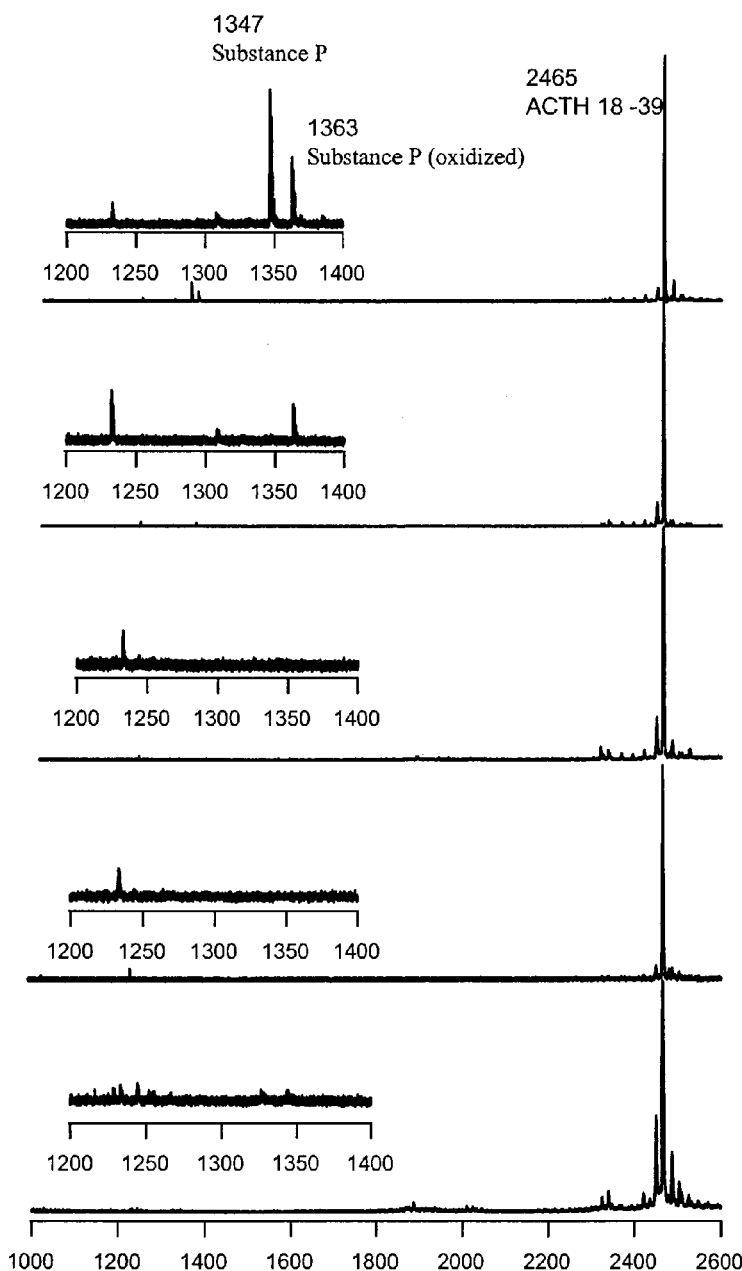
FIG. 7A is from the analysis of a 10:1 mole ratio of ACTH to substance P, with 210 fmol substance P deposited on the target.
FIG. 7B is a 100:1 mole ratio, with 21 fmol substance P deposited.
FIG. 7C is a 1000:1 mole ratio, with 2 fmol substance P.
FIG. 7D is a 1000:1 mole ratio of ACTH to substance P, with 21 fmol substance P.
FIG. 7E is a 1000:1 mole ratio, with 100 fmol substance P.

The detection of a minor peptide component in the presence of high concentration of other components can be a challenging task. Although MALDI-TOF-MS is suitable for the analysis of complex mixtures, it is susceptible to ion suppression effects, which result in reduced detection sensitivity for minor components of the mixture. This effect was demonstrated in FIG. 7, which displays that direct MALDI-MS analysis of substance P (the minor component) in the presence of increasing amounts of Adrenocorticotropic Hormone (ACTH) 18-39. As shown in FIG. 7A, substance P (m/z at 1347, along with the oxidized derivative at m/z 1363) was easily detected by direct MALDI-TOF-MS in a ten-fold mole excess of ACTH 18-39. The substance P peak was still clearly seen at 100-fold excess of ACTH (FIG. 7B). However, at a 1000-fold excess of ACTH 18-39, the signal for substance P was totally suppressed (FIG. 7C). Even at higher loadings of 21 or 100 fmol of substance P (FIGS. 7D and 7E), the presence of 1000-fold excess of ACTH 18-39 continuously suppressed the signal for substance P.

This simple peptide mixture was then subject to HPLC separation, followed by sample collection using the HPLC-MALDI interface of this invention as described above. Samples were prepared at various ratios (1:100 to 1:1,000,000) of substance P: ACTH 18-39 and separated on RP $C_{18}$ columns of different dimensions (0.3×150 mm, 1.0×150 mm and 2.1×150 mm). On the 1.0×150 mm (microbore) $C_{18}$ column, substance P could be detected in the presence of $10^5$ excess of ACTH 18-39 (FIG. 8D). A total of 5 µg of peptide sample were injected on the column, since this amount corresponds to the manufacture's specified capacity for the column. Note that an impurity peak (m/z 2317) originating from the ACTH sample was also collected in the fraction corresponding to the collection of substance P. However, the ability to fractionate the majority of the suppressing compound (i.e., ACTH 18-39) allows for substance P to be detected in the presence of a significantly higher proportion of interfering components, as compared to direct MALDI analysis.

The detection of low abundant substance P in the mixture was dependent upon the amount of sample present for MALDI analysis, which was dependent on the sample loading on the HPLC column. A larger column allowed for higher sample loading, and therefore higher dynamic range for the detection of low-abundant analytes. For example, a nanobore capillary column (0.3×150 mm) had a capacity of 0.5 µg. When tested, the mixture of substance P and ACTH 18-39 revealed a detectable substance P signal only up to 1:1000. Although this is an improvement over the dynamic range seen in direct MALDI, this is significantly lower than the larger column. Larger columns allow for higher sample loading, therefore sufficient amounts of sample for the minor components become available for analysis.

This example illustrates that the HPLC-MALDI interface of this invention exhibits a broad dynamic range detection advantage.

Example 4

Characterization of a Protein Mixture

Figure 9A:
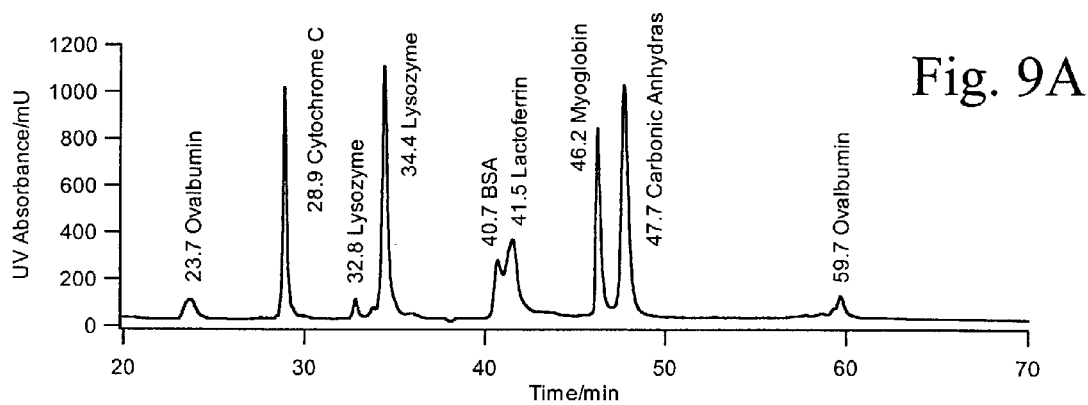
FIG. 9A is the UV trace monitored for the separation of the protein mixture.
Figure 9B:
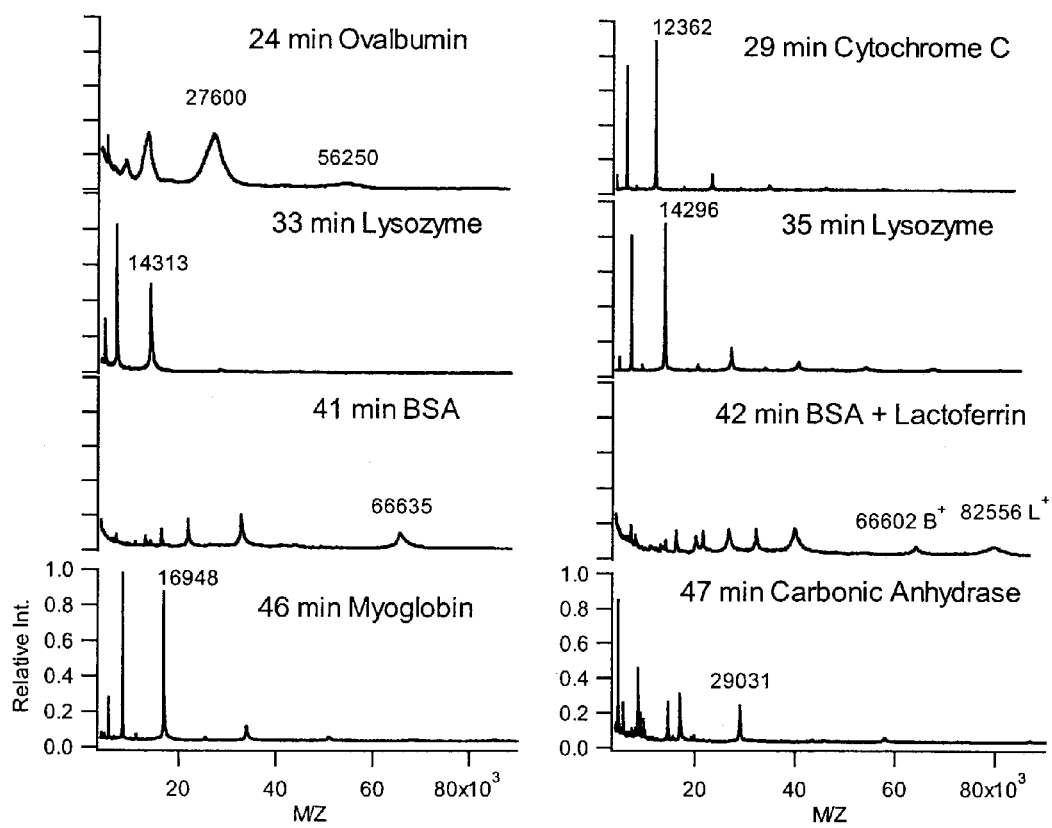
FIG. 9B shows selected MALDI spectra recorded from fractions containing the proteins.
Figure 10A:
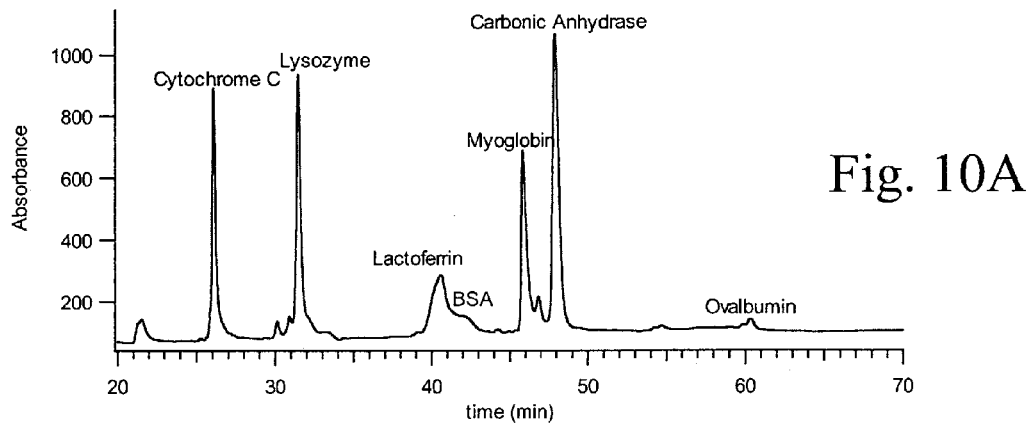
FIG. 10A is a UV trace of a 7-protein mixture separated by HPLC.
Figure 10B:
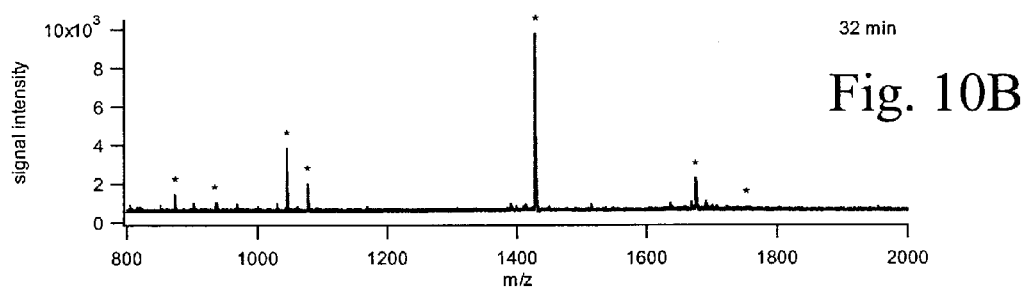
FIGS. 10B, 10C and 10D are representative examples of MALDI-MS spectra recorded following on-target tryptic digestion of a collected protein fraction.
Figure 10C:
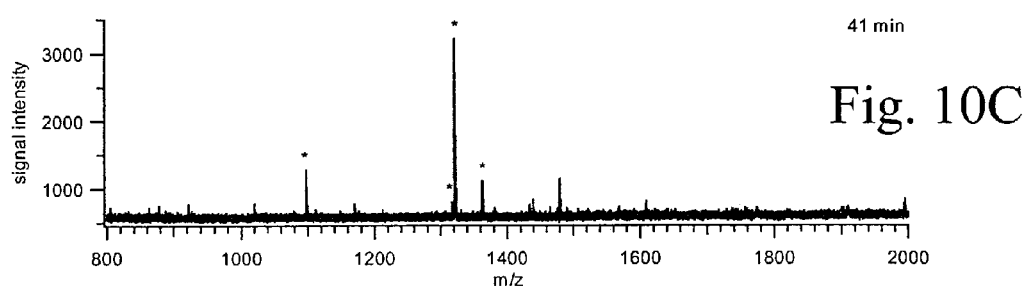
Figure 10D:
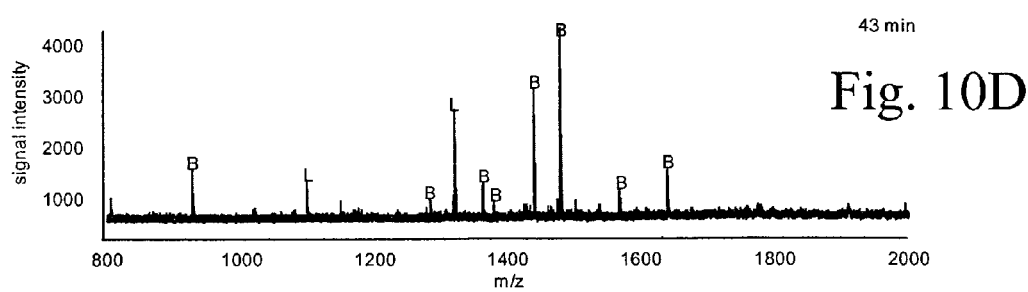

A mixture of seven proteins was subjected to separation on a 1.0×150 mm $C_8$ column, at a flow rate of 40 µl/min. The proteins ranged in molecular weight from 12 kDa (cytochrome c) to 85 kDa (lactoferrin), and the total injection amount was about 1 µg of each. The resulting UV trace, monitored at 214 nm is shown in FIG. 9A. MALDI analysis of the deposited fractions revealed that each of these proteins was detected by MS. The MS signals from the analysis of the fractions containing the signals are displayed in FIG. 9B. These results demonstrate the ability to detect large proteins using the on-line concentrator and fraction deposition interface. It is also seen that the use of heat to dry solvent does not hinder the MALDI-MS detection of these larger proteins.

Example 5

Rapid Proteome Analysis of Water Soluble Components of E. Coli K12

This example illustrates how the higher dynamic range afforded by the LC-MALDI interface of this invention allows for an increase in the identification of individual analytes from a complex mixture of biological origin.

A 6 mg sample of lyophilized *E. coli* cells (ATCC #47076) was suspended in 2 ml of 10 mM Tris-HCl buffer (pH 7.85), and sonicated for 1 min with a Probe tip sonicator (Branson Sonifier 450, Branson Ultrasonics, Danbury, Conn., USA). The suspension was centrifuged at 11750 g for 10 min, and the supernatant was retained. This extraction process was repeated 3 times, the extracts were pooled, and then filtered through Microcon-3 filters (Millipore) with 3000-Da molecular mass cutoff, and finally concentrated to 1.0 ml by Speed-Vac. Dithiothreitol was added to 1 mM final concentration and then incubated at 37° C. for half an hour, followed by the addition of 2 mM (final concentration) iodo acetamide, with incubation in a dark place for 30 min. Finally, a small amount of trypsin solution (1:100 mass ratio of the total protein content) was added to the protein mixture and incubated at 37° C. for overnight. The resulting peptide mixture was subjected to HPLC-MALDI-TOF MS integrated separation and analysis. A 60 µl sample of the peptide mixture (ca 0.4 µg/µl) was loaded on the 2.1×150 mm $C_8$ column and collected from 1 min to 90 min, 1 min per well, onto a 100 well gold surface plate from Applied Biosystems. The collected sample spots were analyzed by MALDI-MS and strong peaks observed in MS analysis were subject to MS/MS analysis to produce fragment ion spectra. The resulting spectra were used to identify the unknown protein components using the MASCOT search program, available on the internet at the Matrix Science Ltd. website (matrix-science.com). Those peptides giving significant matches are summarized in Table 1. Of the 598 MS/MS spectra generated from analysis of this sample, 254 resulted in significant matches to the protein database, and these peptides are from 133 unique proteins of *E. coli* bacteria source.

To further test the dynamic range detection advantage of HPLC-MALDI interface, a capillary $C_{18}$ column (0.3×150 mm) was injected with 2.5-µl tryptic bacteria peptide mixture (ca 0.4 µg/µl) and subject to HPLC-MALDI-MS analysis. Using the same protocol as above, the collected sample spots were subject to MS and MS/MS analysis, submitting the fragment ion spectra to MASCOT for protein identification. As summarized in Table 1, the results of this experiment yield much less peptides that gave significant matches to the protein database. This confirms the conclusion that a larger amount of sample that can be separated on larger columns (at higher optimal flow rates) results in a higher dynamic range.

Example 6

Direct Digestion on the MALDI Plate

This example illustrates the ability to apply post-separation sample workup following fractionation and analyte enrichment with the present invention.

The seven-protein standard mixture (from Example 4) was subject to HPLC separation and dried fractions were collected on the commercial MALDI target having wells of 2.4 mm diameter. A total of 1.1 µg of each protein was used for the separation. Following sample collection, 1 µl of 50 mM ammonium bicarbonate and 1 µl of 0.3 µg/µl trypsin was added to each well. The MALDI plate was incubated for 1.5 hours at room temperature in a high humidity environment, to prevent the solution from drying up. After incubation, the remaining solution was allowed to dry in ambient atmosphere. A MALDI matrix solution was added to the wells and the samples were then subjected to MALDI analysis. FIGS. 10A-10D display the UV chromatogram from analysis of the seven-protein mixture, along with three representative MALDI-MS spectra from the analysis of the on-target tryptic digestion of the samples. From the obtained MALDI spectra, the highest intensity peaks were submitted to the MASCOT program to query the SwissProt database. For all seven proteins, the MASCOT search program identified the correct protein as the top candidate. Table 2 summarizes the MASCOT search results obtained from analysis of the tryptic digests. These results illustrate the ability to perform subsequent manipulations of collected samples from the on-line concentrator deposition apparatus. Note that the direct digestion of proteins in the presence of acetonitrile (from the effluent) would otherwise hinder the digestion process. Elimination of solvent with the on-line concentrator allows for immediate workup without the need for further solvent elimination. In addition, solvent elimination leads to increased sample concentration in a small confined area, which again aids in subsequent reaction steps, as well as in improved detection sensitivity.

TABLE 2

Mascot search results from MALDI MS analysis of on-target tryptic digests of proteins, following HPLC separation, with fraction collection by the HPLC-MALDI interface

| fraction # | protein identity | # peptides submitted | MOWSE score | P value |
|---|---|---|---|---|
| 27 | cytochrome c | 5 | 84 | 3.E−09 |
| 32 | lysozyme c | 7 | 84 | 3.E−09 |
| 41 | lactoferrin | 7 | 48 | 2.E−05 |
| 42 | serum albumin precursor | 4 | 51 | 4.E−06 |

TABLE 1

Summary for HPLC-MALDI-QTOF MS/MS analysis of water-soluble protein components of *E. coli* bacteria (ATCC47076)

| | HPLC-MALDI Interface | Q-TOF MS/MS Analysis Result |
|---|---|---|
| Load amount: | 24 µg | 598 ms/ms spectra collected |
| HPLC Column: | Analytical RP 2.1 × 150 mm $C_8$ | 256 peptide hits |
| MALDI Target: | 1 × 10 well (Ø2.4 mm) Gold | 133 unique protein identifications |
| Load amount: | 1 µg | 167 ms/ms spectra collected |
| HPLC Column: | Microbore RP 0.3 × 150 mm $C_{18}$ | 77 peptide hits |
| MALDI Target: | 10 × 10 well (Ø0.8 mm) Stainless Steel | 45 unique protein identifications |

TABLE 2-continued

Mascot search results from MALDI MS analysis of on-target tryptic digests of proteins, following HPLC separation, with fraction collection by the HPLC-MALDI interface

| fraction # | protein identity | # peptides submitted | MOWSE score | P value |
| --- | --- | --- | --- | --- |
| 43 | serum albumin precursor | 7 | 88 | 2.E−09 |
| 46 | myoglobin | 5 | 94 | 4.E−10 |
| 49 | carbonic anhydrase | 5 | 65 | 3.E−07 |
| 61 | ovalbumin | 4 | 41 | 8.E−05 |

All publications mentioned in this specification are indicative of the level of skill of those skilled in the art to which this invention pertains. All publications are herein incorporated by reference to the same extent as if each individual publication was specifically and individually indicated to be incorporated by reference.

The terms and expressions in this specification are, unless otherwise specifically defined herein, used as terms of description and not of limitation. There is no intention, in using such terms and expressions, of excluding equivalents of the features illustrated and described, it being recognized that the scope of the invention is defined and limited only by the claims which follow.

What is claimed is:

1. An apparatus for concentrating and collecting one or more analytes in a flowing liquid stream of a carrier solvent composed of one or more solvent components, comprising:
    a transfer tube which forms a bore having an inlet and an outlet, the inlet being adapted to accept the flowing liquid stream;
    a heating device for heating the liquid stream in the transfer tube, the heating device being a heating coil, heated tape, or heated block positioned around a portion of the transfer tube to provide a heated portion of the transfer tube;
    the transfer tube having a vertical portion forming an extension line which extends below the heated portion of the transfer tube and forms the outlet, the outlet being adapted to form continuously replaced, hanging droplets of the liquid stream;
    the heating device being temperature adjustable for heating the liquid stream in the transfer tube to a temperature sufficient to cause partial evaporation of the carrier solvent from the hanging droplets but not exceeding the boiling point of the carrier solvent;
    a collection device mounted in a horizontal plane below the outlet of the transfer tube for collecting the droplets;
    a device for heating the collection device to a temperature sufficient to cause further evaporation of the carrier solvent; and
    a robot device adapted for X-Y or X-Y-Z motion, with X-Y being in the horizontal plane and Z being in a vertical plane, associated with one or both of the collection device and the transfer tube such that the apparatus achieves relative X-Y or X-Y-Z motion of the transfer tube and the collection device.

2. The apparatus of claim 1, wherein the robot device is programmable for the motion and the timing of the motion.

3. The apparatus of claim 1, wherein the device for heating the collection device is temperature adjustable, and wherein the temperature of the collection device is at or above the boiling point of the least volatile solvent component.

4. The apparatus of claim 3, wherein the device for heating the collection device uses one or more of a heating coil, heated tape, or heated block.

5. The apparatus of claim 1, wherein the transfer tube is formed from or in contact with a heat conductive material, wherein the outlet of the transfer tube is formed from or includes a material which reduces the surface tension of the droplet, and wherein the transfer tube comprises either one or more aligned sections of tubing each forming a bore therethrough, or a block formed with one or more aligned channels each forming a bore therethrough.

6. The apparatus of claim 5, wherein the outlet of each bore has a diameter between about 5 and 500 μm.

7. The apparatus of claim 5, wherein the outlet of each bore has a diameter between about 50 and 200 μm.

8. The apparatus of claim 2, wherein the collection device is formed from or uses a material which is heat conductive and which reduces analyte adsorption, and wherein the collection device is formed with a plurality of spaced structures for confining and retaining the droplets.

9. The apparatus of claim 8, wherein the collection device is a plate or target and the spaced structures are wells.

10. The apparatus of claim 1, which further comprises a gas drying device adapted to direct a non-reactive drying gas at one or both of the outlet of the transfer tube and the collection device.

11. The apparatus of claim 10, wherein the gas drying device is adapted to heat the drying gas.

12. The apparatus of claim 11, wherein the gas drying device is adapted to adjust one or both of the temperature and the flow rate of the drying gas.

13. The apparatus of claim 1, which further comprises a device for dislodging the hanging droplets from the outlet.

14. The apparatus of claim 13, wherein the device for dislodging the droplets is adapted to dislodge the droplets piezoelectrically, electrically, ultrasonically, magnetically, using a pulsed non-reactive gas, or by blotting the droplet onto the collection device.

15. The apparatus of claim 1, which further comprises a housing or exhaust system to remove or contain the evaporated carrier solvent.

16. The apparatus of claim 2, which further comprises a detector directed to respond to the one or more analytes in the liquid stream, and wherein the timing of the motion of the robotic device is controlled in relation to detected analytes.

17. The apparatus of claim 9, wherein the collection device is a target for laser desorption ionization formed with a plurality of wells having openings sized between about 0.2 and 5 mm in diameter.

18. The apparatus of claim 1 wherein the inlet is adapted to receive the effluent from a liquid chromatograph or a flow injection system.

19. A method for concentrating and collecting one or more analytes in a flowing liquid stream of a carrier solvent composed of one or more solvent components, comprising:
    providing a transfer tube which forms a bore having an inlet and an outlet, the inlet being adapted to accent the flowing liquid stream, and the outlet being adapted to form continuously replaced, hanging droplets of the liquid stream;
    providing a heating device for heating the liquid stream, the heating device being a heating coil, heated tape, or heated block positioned around a portion of the transfer tube to provide a heated portion of the transfer tube;
    introducing the liquid stream into a the transfer tube;

allowing the liquid stream to flow through the heated portion of the transfer tube into a vertical extension portion of the transfer tube which extends below the heated portion of the transfer tube and forms the outlet;

heating the liquid stream in the transfer tube with the heating device while controlling the temperature of the liquid stream in the transfer tube to a temperature sufficient to cause partial evaporation of the carrier solvent from the hanging droplets without exceeding the boiling point of the carrier solvent;

allowing the droplet to dislodge from the outlet of the transfer tube;

collecting the droplets on a collection device mounted in a horizontal plane below the outlet of the transfer tube;

moving one or both of the collection device and the transfer tube in X-Y or X-Y-Z directions, with X-Y being in the horizontal plane and Z being in a vertical plane, to achieve relative X-Y or X-Y-Z motion of the transfer tube and the collection device so as to collect discrete fractions on the collection device; and heating the collection device to a temperature sufficient to cause further evaporation of the carrier solvent from the collected droplets.

20. The method of claim 19, wherein a programmable robotic device is used for the motion and the timing of the motion.

21. The method of claim 19, wherein one or both of the heating steps is temperature adjustable, and wherein the collection device is heated to a temperature which is at or above the boiling point of the least volatile solvent component.

22. The method of claim 19, wherein the transfer tube is formed from or in contact with a heat conductive material, wherein the outlet of the transfer tube is formed from or includes a material which reduces the surface tension of the droplet, and wherein the transfer tube comprises either one or more aligned sections of tubing each forming a bore therethrough, or a block formed with one or more aligned channels each forming a bore therethrough.

23. The method of claim 22, wherein the outlet of each bore has a diameter between about 5 and 500 µm.

24. The method of claim 19, wherein the outlet of each bore has a diameter between about 50 and 200 µm.

25. The method of claim 19, wherein the collection device is formed from or uses a material which is heat conductive and which reduces analyte adsorption, and wherein the collection device is formed with a plurality of spaced structures for confining and retaining the droplets.

26. The method of claim 25, wherein the collection device is a plate or target and the spaced structures are wells.

27. The method of claim 19, which further comprises directing non-reactive drying gas at one or both of the hanging droplets and the collection device.

28. The method of claim 27, which includes heating the drying gas.

29. The method of claim 28, which includes adjusting one or both of the temperature and the flow rate of the drying gas.

30. The method of claim 19, which further comprises mechanically dislodging the hanging droplets from the outlet.

31. The method of claim 30, wherein the hanging droplets are dislodged piezoelectrically, electrically, ultrasonically, magnetically, using a pulsed non-reactive gas, or by blotting the droplet onto the collection device.

32. The method of claim 19, which further comprises removing or containing the evaporated carrier solvent.

33. The method of claim 21, which further comprises detecting the one or more analytes in the liquid stream and controlling the timing of the motion in response to the detected analytes.

34. The method of claim 26, wherein the collection device is a target for laser desorption ionization formed with a plurality of wells having openings sized between about 0.2 and 5 mm in diameter.

35. The method of claim 19, wherein the flowing liquid stream is the effluent from a liquid chromatograph or a flow injection system.

* * * * *